United States Patent
Rydsund

(10) Patent No.: US 10,034,550 B2
(45) Date of Patent: Jul. 31, 2018

(54) SOUND DAMPENING DEVICE

(71) Applicant: ARTEX AB, Mjölby (SE)

(72) Inventor: Mats Rydsund, Hägersten (SE)

(73) Assignee: ARTEX AB, Mjölby (SE)

(*) Notice: Subject to any disclaimer, the term of this patent is extended or adjusted under 35 U.S.C. 154(b) by 308 days.

(21) Appl. No.: 14/786,332

(22) PCT Filed: Apr. 17, 2014

(86) PCT No.: PCT/SE2014/050478
§ 371 (c)(1),
(2) Date: Oct. 22, 2015

(87) PCT Pub. No.: WO2014/175809
PCT Pub. Date: Oct. 30, 2014

(65) Prior Publication Data
US 2016/0066699 A1    Mar. 10, 2016

(30) Foreign Application Priority Data
Apr. 23, 2013 (SE) ...................... 1300295

(51) Int. Cl.
*A47C 21/04* (2006.01)
*G10K 11/162* (2006.01)
(Continued)

(52) U.S. Cl.
CPC ............ *A47C 19/022* (2013.01); *A47C 31/00* (2013.01); *F24F 13/24* (2013.01); *G10K 11/161* (2013.01);
(Continued)

(58) Field of Classification Search
CPC .. A47C 21/044; A47C 21/042; G10K 11/161; G10K 11/162; G10K 11/172
(Continued)

(56) References Cited

U.S. PATENT DOCUMENTS 3,724,172 A    4/1973  Wood
3,795,092 A *  3/1974  Schwartz ............... B01D 46/10
                                                      55/473
(Continued)

FOREIGN PATENT DOCUMENTS

EP    0348011 A2    12/1989
EP    0380660 A1    8/1990
(Continued)

OTHER PUBLICATIONS

Supplemental European Search report and Written Opinion dated Nov. 21, 2016 in corresponding EP Application No. 14788109.

*Primary Examiner* — Jeremy Luks
(74) *Attorney, Agent, or Firm* — Knobbe, Martens, Olson & Bear, LLP

(57) ABSTRACT

The invention relates to a sound dampening device (1) comprising a frame (2), a rear layer (4) and a front layer (6) arranged on opposite sides of the frame (2), such that the frame (2), the rear layer (4) and the front layer (6) forms an enclosed space, wherein a first sound absorbing layer (8) is arranged between the rear layer (4) and the front layer (6). A cavity (10) is formed between the rear layer (4) and the first sound absorbing layer (8) and an air purifying device (12) is arranged in fluid communication with said cavity (10), such that purified air from the air purifying device (12) is supplied to the cavity (10) via an inlet (14) and is discharged through at least one opening (16) in the first sound absorbing layer (8) and at least one output zone (18) in the front layer (6).

20 Claims, 6 Drawing Sheets

(51) Int. Cl.
*G10K 11/172* (2006.01)
*A47C 19/02* (2006.01)
*G10K 11/16* (2006.01)
*F24F 13/24* (2006.01)
*A47C 31/00* (2006.01)
*A61L 9/20* (2006.01)

(52) U.S. Cl.
CPC .......... *G10K 11/162* (2013.01); *G10K 11/172* (2013.01); *A61L 9/20* (2013.01); *A61L 2209/14* (2013.01)

(58) Field of Classification Search
USPC .................................................. 181/224, 225
See application file for complete search history.

(56) References Cited

U.S. PATENT DOCUMENTS

| | | | |
|---|---|---|---|
| 3,861,894 A | 1/1975 | Marsh | |
| 3,935,803 A * | 2/1976 | Bush | F24F 3/1607 454/189 |
| 4,006,604 A | 2/1977 | Seff | |
| 4,856,242 A | 8/1989 | Baloga et al. | |
| 5,074,116 A | 12/1991 | Kadotani et al. | |
| 5,129,928 A * | 7/1992 | Chan | F24F 3/1603 55/385.1 |
| 5,830,058 A | 11/1998 | Rosjo | |
| 6,261,332 B1 * | 7/2001 | Richard | B01D 46/0023 55/385.1 |
| 6,296,075 B1 | 10/2001 | Gish et al. | |
| 8,122,540 B2 * | 2/2012 | Ardis | A47C 21/044 5/284 |
| 2004/0009746 A1 | 1/2004 | Korman | |
| 2004/0242148 A1 | 12/2004 | Schmid et al. | |
| 2007/0128998 A1 | 6/2007 | Mizutani et al. | |
| 2011/0100749 A1 | 5/2011 | Nonogi et al. | |
| 2011/0284689 A1 | 11/2011 | Thomas et al. | |
| 2012/0155669 A1 | 6/2012 | Carme | |

FOREIGN PATENT DOCUMENTS

| | | |
|---|---|---|
| GB | 667055 A | 2/1952 |
| JP | 2010-116118 A | 5/2010 |
| WO | 03/104582 A2 | 12/2003 |
| WO | 2006/062878 A2 | 6/2006 |

* cited by examiner

SOUND DAMPENING DEVICE

CROSS-REFERENCE TO RELATED APPLICATIONS

This application is the U.S. National Phase under 35. U.S.C. § 371 of International Application PCT/SE2014/050478, filed Apr. 17, 2014, which claims priority to Swedish Patent Application No. 1300295-1, filed Apr. 23, 2013. The disclosures of the above-described applications are hereby incorporated by reference in their entirety.

TECHNICAL FIELD

The present invention relates to a sound dampening device. The invention may be attributed to the manufacturing industry of sound dampening devices.

BACKGROUND

Various devices are today used to improve the indoor environment in for example offices, public buildings, schools, hospitals and exhibition areas or similar. The indoor environment may affect peoples' health, their quality of life, comfort, ability to learn and productivity. This is specifically a fact in colder climates where people tend to spend more time indoors. Factors that may affect the indoor environment are air quality, thermal comfort, acoustic properties and the visual quality.

Poor acoustic properties in an indoor environment may specifically affect people's cognitive and communicative abilities. Consequences of poor acoustic environments may be attention problems, concentration problems, reduced ability to learn, lower quality of performed work and lower productivity. At higher sound levels there might also be a risk of temporary or permanent hearing impairment, tinnitus, health problems and stress.

The indoor air quality may also affect people's health. Air pollutants, particles, allergens, humidity, mould, bacteria and virus are examples of elements that may be a health hazard. Poor air quality may cause asthma, allergies, symptoms in the eyes, the nose and on the skin, fatigue and headache. Such symptoms will, naturally, also have an impact on cognitive and communicative abilities.

Various devices are often used to each solve a separate problem relating to the indoor environment. In order to improve the acoustic properties in a room acoustic screens, panels and sound dampening partition walls may be used. Ventilation and air conditioning units may be used to improve the thermal comfort and air purifiers may be used to improve the air quality. While these devices solve one problem, they may cause another problem. For example, a separate air purifier might be visually disturbing and cause unpleasant air flows, draught, high noise levels and might even be standing in the way. Some sound absorbing solutions may also cause problems, such as hindering ventilation and collecting of dust, particles and microorganisms. Also, in order to improve the air quality in a whole room, an air purifier needs to purify a large air volume and thus is needed a powerful fan.

There are some examples of solutions which try to combine several functions in order to improve the indoor environment. Document EP0380660 describes a radiation air-conditioner in the form of a partition wall, which can be freely moved in order to handle the problem with unevenly distributed heat loads in a closed office. The air-conditioner comprises a panel with a plurality of thermoelectric elements and heat exchanger means and fan means installed inside the panel. This is however a complex and costly solution which complicates maintenance and service of the air-conditioner.

Document SE533460 discloses an arrangement for purifying large air volumes where fans and air filters are combined with sound absorbers for dampening noise from the fans. The arrangement is large and bulky.

Despite known solutions in the area there is a need to further develop a simple, cost-effective solution for improving the indoor environment.

SUMMARY OF THE INVENTION

The object of the present invention is to provide a sound dampening device, which improves the indoor environment in multiple ways.

A further object of the invention is to provide a sound dampening device, which achieves a local environment with purified air.

Yet another object of the invention is to provide a sound dampening device, which is cost-effective.

These objects are achieved by the sound dampening device of the initially mentioned kind, which is characterized by the features specified in the characterizing part of claim 1.

The sound dampening device according to the invention comprises a frame, a rear layer and a front layer arranged on opposite sides of the frame, such that the frame, the rear layer and the front layer forms an enclosed space. A first sound absorbing layer is also arranged between the rear layer and the front layer wherein a cavity is formed between the rear layer and the first sound absorbing layer. By arranging an air purifying device in fluid communication with the cavity, such that purified air from the air purifying device is supplied to the cavity via an inlet and is discharged through at least one opening in the first sound absorbing layer and at least one output zone in the front layer, an air purifying function integrated with a sound dampening function is achieved. Both the sound absorbing layer and the cavity dampen sounds from the environment as well as from the air purifying device, which results in a very efficient sound dampening. By discharging purified air through the front layer pure air is discharged where it is actually needed and a local environment with purified air is achieved. This is very difficult to achieve with common air purifiers for purifying a whole room, where a very large air volume needs to be purified. Also, by focusing on improving the local environment a smaller air volume needs to be purified and the capacity of the air purifying device can be minimized, which results in a cost-effective air purifying sound dampening device.

According to an aspect of the invention an air permeable distribution layer is arranged in the at least one opening in the first sound absorbing layer, such that the purified air is discharged through the front layer via the distribution layer. Alternatively, the distribution layer is arranged between the cavity and the first sound absorbing layer. The distribution layer may also be arranged between the cavity and the first sound absorbing layer as well as in the at least one opening in the first sound absorbing layer. Air always chooses the way with less flow resistance and the distribution layer and the rear layer are configured such that the flow resistance in the distribution layer is less than in the rear layer. This way, when purified air is supplied to the cavity and a pressure builds up inside the cavity, the purified air is distributed throughout the distribution layer and is discharged through the at least one output zone in the front layer.

The distribution layer may comprise a cellular plastic, such as foam or a polyester resin, with an open cell structure and low density. A cellular plastic is a type of plastic containing numerous cells or pores disposed uniformly throughout its mass. An open cell structure means that the cells are connected to each other, which make the material soft, light and airy. A closed cell structure means that each cell is completely surrounded by a solid material and the cells are thus separated from each other. A material with an open cell structure typically has a higher permeability than a material with a closed cell structure. The distribution layer may comprise a material with a cell diameter between 2000 to 3500 micrometers. The open cell structure and the cell diameter results in a high permeability/porosity of the distribution layer, which causes a low flow resistance and thus a limited pressure drop of the airflow when passing through the distribution layer. The flow resistance and the pressure drop cause the purified air to spread and to be distributed within and throughout the distribution layer. This way, the flow area through which the purified air is discharged is larger than the cross sectional area of the inlet to the cavity and a substantially even distribution of purified air is achieved over a larger area. By having a larger outlet area than inlet area, the purified air is discharged with a lower flow rate than when supplied to the cavity through the inlet. A low flow rate is advantageous in that draught is avoided and a comfortable local environment with purified air is achieved. The low flow resistance in the distribution layer also means that the air purifying device can operate with low power and still achieve the desired flow rate, which minimizes the vibrations and noise from the air purifying device itself. The distribution layer may comprise any other material with equivalent properties relating to resistance and permeability. The thickness of the distribution layer may be 10-25 millimeters.

Permeability is defined as a measure of the ability of a material to transmit fluids at a certain loss of pressure. High permeability means that a larger volume of fluid may be transmitted per square meter of the material and unit of time.

According to an aspect of the invention, the distribution layer comprises air channels perpendicular to the extension of the front layer. The purified air is led into the channels and flows in the direction towards the front layer. This way, the air flow at the output of the distribution layer and at the at least one output zone of the front layer, is directed substantially perpendicularly to the extension of the front layer. A substantially laminar air flow is thus achieved at the output of the distribution layer and at the output of the front layer.

According to an aspect of the invention, the front layer has a weight per area unit of 150-350 $g/m^2$. This relatively low weight corresponds to a high permeability and low flow resistance. The front layer may comprise stitched polyester or any other fabric with the same high permeability and low flow resistance. This way, the front layer causes a low resistance and the purified air is discharged through the front layer with an optimal low speed. The front layer may have a thickness of 0.2-3 millimeters.

According to an aspect of the invention, the first sound absorbing layer preferably has a weight per area unit of 1000-1500 $g/m^2$. This relatively high weight corresponds to a low permeability and high flow resistance. The first sound absorbing layer and the distribution layer are configured such that the permeability is higher and the flow resistance is lower in the distribution layer than in the first sound absorbing layer. This way, the air chooses to flow through the opening in the sound absorbing layer and/or the distribution layer, where the permeability is higher. The first sound absorbing layer may comprise pressed polyester fibre. The thickness of the first sound absorbing layer is between 10-50 millimeters, preferably 13-20 millimeters.

According to an aspect of the invention, the air purifying device comprises at least one filter unit and fan means. The air purifying device preferably comprises a housing inside which the fan means is arranged and the at least one filter unit is arranged at the inlet of the housing, such that polluted air from the surroundings first enter the at least one filter unit by suction of the fan means and is subsequently supplied to the cavity by the fan means. The fan means comprises a motor and a rotating arrangement of vanes or blades.

The inlet to the cavity preferably comprises an aperture in the front layer. The air purifying device is then suitably tightly arranged at the front layer, such that it covers the aperture. The air purifying device is preferably arranged such that the housing covers the aperture in the front layer and such that the fan means is arranged in the inlet to the cavity. Alternatively, the inlet to the cavity comprises an aperture in the rear layer or the frame. Thus, the air purifying device may be tightly arranged at the rear layer or at the frame respectively. Since the air purifying device preferably is arranged on the outer side of the front layer, rear layer or the frame, a sound dampening device is achieved, which facilitates maintenance and service.

According to an aspect of the invention, a second sound absorbing layer is arranged at an outer side of the rear layer. The second sound absorbing layer suitably consists of a fabric with a polyether foam coating. This way, the sound dampening function of the sound dampening device is improved.

According to an aspect of the invention, an air permeable padded layer is arranged on the outer side of the front layer. Alternatively an air permeable padded layer is arranged between the first sound absorbing layer and the front layer. This way, the sound dampening device is soft and comfortable to leans against. The padded layer may comprise a cellular plastic, such as foam or a polyester resin, with an open cell structure and low density. The padded layer may comprise a material with a cell diameter between 1500 to 2500 micrometers. The open cell structure and the cell diameter results in a high permeability/porosity and the padded layer barely affects the flow rate of the purified air. The padded layer may comprise any other material with equivalent properties relating to flow resistance and permeability. The thickness of the padded layer may be 20-50 millimeters.

According to an aspect of the invention a regulating means for regulating the air flow from the air purifying device is arranged on an outer side of the front layer. Alternatively the regulating means is arranged on an outer side of the frame or the rear layer. The user of the sound dampening device may thereby regulate the air flow being discharged through the front layer and the user can also completely turn off the air purifying device. This way is achieved a flexible and user-friendly sound dampening device.

The rear layer preferably comprises an impermeable material, preferably a wooden board, cardboard, fibre board or similar. Alternatively, the rear layer may comprise a pressed polyester fibre or similar material with a weight per area unit of 1000-1500 $g/m^2$. This weight corresponds to a low permeability and purified air will thus not pass through the rear layer.

According to an aspect of the invention the sound dampening device constitutes a partition wall or an acoustic screen. The sound dampening device is then preferably arranged on a desk or by a desk, in for example an office. The sound dampening device is preferably arranged such that the air purifying device is positioned under the desktop. This way, the sound from the air purifying device is further dampened by the desktop. When arranged at a desk, the at least one output zone in the front layer is arranged substantially at the level/height of the head of a person sitting or standing at the desk. This way, the purified air is discharged in the vicinity of the persons face and a good and healthy air quality is achieved in the person's local environment. The sound dampening device constituting an acoustic screen may have a width of 800-2200 millimeters and a height of 600-1000 millimeters. The thickness of the sound dampening device may be 30-60 millimeters.

According to an aspect of the invention the sound dampening device comprises an air cooling device. By cooling the air before discharge through the front layer the air gets heavier and this way is controlled that the discharged air falls downwards rather than rises upwards. This ensures that the purified air is collected where it does the most good.

These objects are also achieved by the headboard device comprising the sound dampening according to claim 15 and the headboard device according to claim 16.

According to an aspect of the invention the headboard device comprises a frame, a rear layer and a front layer arranged on opposite sides of the frame, such that the frame, the rear layer and the front layer forms an enclosed space, wherein a first intermediate layer is arranged between the rear layer and the front layer. A cavity is formed between the rear layer and the intermediate layer and an air purifying device is arranged in fluid communication with said cavity, such that purified air from the air purifying device is supplied to the cavity via an inlet and is discharged through at least one opening in the intermediate layer and at least one output zone in the front layer. This way is achieved a headboard which purifies air and thus creates a local environment with purified air.

According to an aspect of the invention, the first intermediate layer is a sound absorbing layer. This way is achieved a headboard with an integrated air purifying function and a sound dampening function.

Preferably, an air permeable distribution layer is arranged in the at least one opening in the intermediate layer, such that the purified air is discharged through the front layer via the distribution layer. The distribution layer may comprise air channels perpendicular to the extension of the front layer.

The air purifying device of the headboard device preferably comprises at least one filter unit and fan means.

According to an aspect of the invention an air permeable padded layer is arranged on an outer side of the front layer of the headboard device.

Preferably, a regulating means for regulating the air flow from the air purifying device is arranged on an outer side of the front layer of the headboard device.

The headboard device is preferably arranged by the end of a bed or next to a bed such that the air purifying device is positioned under the bed. The sound from the air purifying device is thus further dampened by the bed. Cold air is heavier than warm air and the air at the floor level in a room is thus colder than the air on a higher level in the room. The difference of temperature in a room may vary between 0.2-2 degrees between different levels. By arranging the headboard device with the air purifying device close to the floor under the bed, colder air will enter the headboard device.

When the purified air is discharged from the headboard device it will fall downwards since it is colder than the surrounding air at the same level and thus has a higher density. This way the natural temperature difference in a room is taken advantage of and it is ensured that the purified air is supplied and stays in the vicinity of the person lying on the bed.

The headboard device may have a width of 700-2200 millimeters and a height of 900-1300 millimeters. The thickness of the headboard device may be 30-250 millimeters.

The headboard may also comprise speakers, sockets for mobile phone chargers, compartments, shelves and/or lightening integrated into the sound dampening device. This way is achieved a functional headboard, which is sound dampening and provides a pure local environment. Good air quality in a bedroom may improve the sleep and thus improves people's health.

Further advantages of the invention appear from the following detailed description.

BRIEF DESCRIPTION OF THE DRAWINGS

In the following, examples of the invention are described with reference to the accompanying drawings, in which.

DETAILED DESCRIPTION OF THE INVENTION

Figure 1:
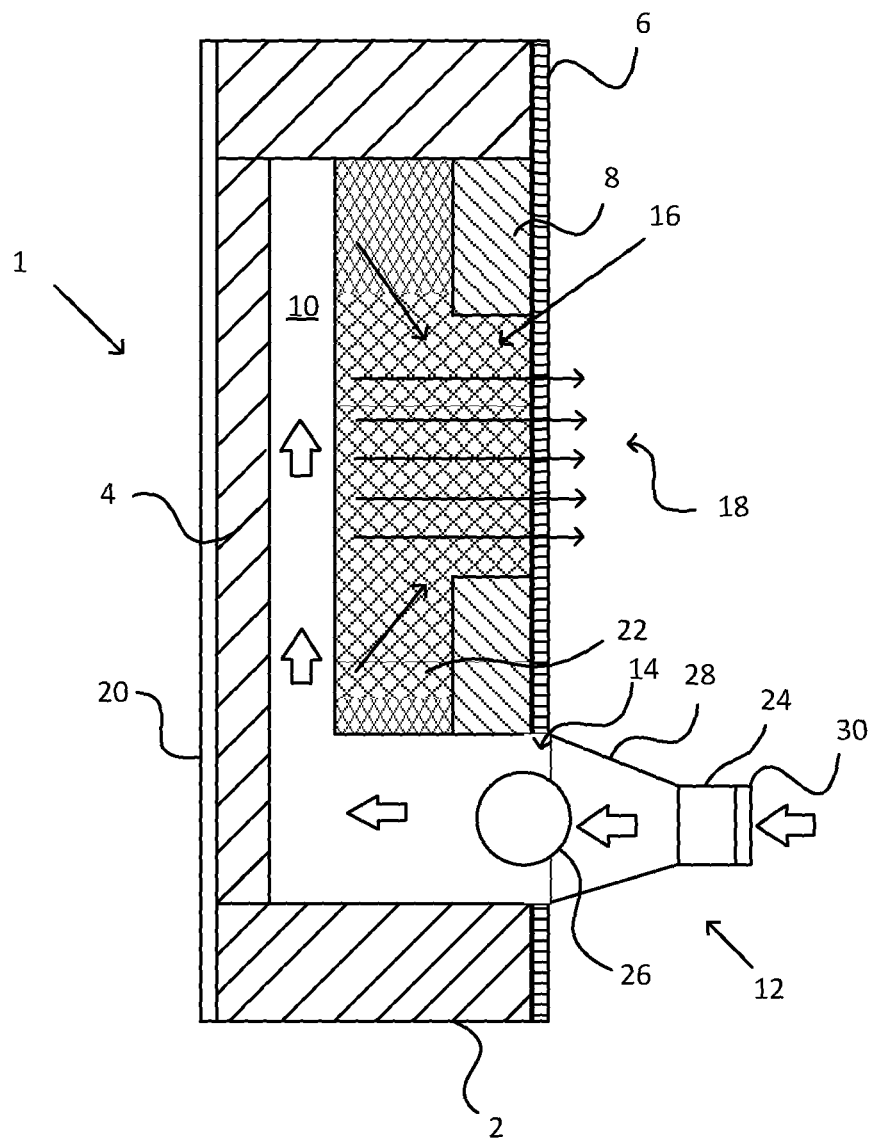
FIG. 1 shows a cross-sectional side view of a sound dampening device according to an embodiment of the present invention.

The present invention will now be described as embodiments. For clarity, the components irrelevant to the invention have been omitted in the drawing. The same details as shown in several drawings may sometimes lack reference numerals, but correspond to those with reference numerals.

FIG. 1 shows a cross-sectional side view of a sound dampening device 1 according to an embodiment of the present invention. The sound dampening device 1 comprises a frame 2, a rear layer 4 and a front layer 6 arranged on opposite sides of the frame 2, such that the frame 2, the rear layer 4 and the front layer 6 forms an enclosed space. A first sound absorbing layer 8 is also arranged between the rear layer 4 and the front layer 6 wherein a cavity 10 is formed between the rear layer 4 and the first sound absorbing layer 8. An air purifying device 12 is arranged in fluid communication with the cavity 10, such that purified air from the air purifying device 12 is supplied to the cavity 10 via an inlet 14 and is discharged through at least one opening 16 in the first sound absorbing layer 8 and at least one output zone 18 in the front layer 6. Polluted air from the environment in which the sound dampening device 1 is arranged is entering the air purifying device 12 and is purified. The purified air is supplied to the cavity 10 through the inlet 14 and when the cavity 10 fills up with air a pressure builds up inside the cavity 10. The pressure inside the cavity 10 then becomes higher than the pressure in the surrounding layers. Air always chooses to flow where there is less flow resistance. In the disclosed embodiment, due to the permeability and thus flow resistance of the rear layer 4 and the first sound absorbing layer 8, the air passes through the at least one opening 16 in the first sound absorbing layer 8 and is discharged through the at least one output zone 18 in the front layer 6. This way, purified air is supplied in the vicinity of the sound dampening device 1 and a local environment with purified air is achieved. Also, the first sound absorbing layer 8 and the cavity 10 cause the sound dampening device 1 to dampen sounds from the environment as well as from the air purifying device 12. This way is achieved a sound dampening device 1, which improves the indoor environment in multiple ways. A pure environment with good acoustic properties can improve people's comfort and health and may result in higher productivity.

The frame 2 preferably comprises wooden beams arranged to form a rectangular frame. Alternatively the frame 2 has a square shape or any other shape. The frame 2 may comprise a lightweight material such as composites, aluminum, fiberglass, or similar.

The front layer 6 has a weight per area unit of 150-350 g/m² which corresponds to a high permeability and low flow resistance. The front layer may comprise stitched polyester or any other fabric with the same low flow resistance and high permeability. This way, the front layer 6 causes a low flow resistance and the purified air is discharged through the front layer 6 with an optimal speed. The thickness of the front layer 6 is between 0.1-4 millimeters, preferably between 0.2-3 millimeters. Alternatively, the front layer 6 comprises an impermeable material with at least one port defining the at least one output zone 18.

The rear layer 4 preferably comprises an impermeable material, preferably a wooden board, cardboard, fibre board or similar. Alternatively, the rear layer 4 may comprise a pressed polyester fibre or similar material with a weight per area unit of 1000-1500 g/m². This weight per area unit corresponds to a low permeability and purified air will thus not pass through the rear layer 4. On an outer side of the rear layer 4, a second sound absorbing layer 20 is arranged. The second sound absorbing layer 20 suitably consists of a fabric with a polyether foam coating. The density of the second sound absorbing layer is between 20-70 kg/m³, preferably between 35-60 kg/m³.

The weight per unit area of the first sound absorbing layer 8 is preferably between 1000-1500 g/m², which corresponds to a high flow resistance and thus low permeability. This way, the air chooses to flow through the opening 16 in the sound absorbing layer 8, where the flow resistance is lower. The first sound absorbing layer 8 may comprise pressed polyester fibre. The first sound absorbing layer 8 may be a wadding of thermal bonded polyester fibre comprising a plurality of micro openings. The thickness of the first sound absorbing layer 8 is between 10-50 millimeters, preferably 13-20 millimeters. The first sound absorbing layer 8 is preferably arranged between the rear layer 4 and the front layer 6, such that it abuts the front layer 6 and the at least one opening 16 in the first sound absorbing layer 8 may have the shape of a rectangle. The at least one opening 16 may have a width between 80-120 centimeters and a height between 15-25 centimeters. Alternatively, the first sound absorbing layer 8 may comprise a plurality of openings 16 with a rectangular shape, a circular shape or any other shape. Due to lower air resistance, the purified air passes through the openings 16 in the first sound absorbing layer 8 and on through the front layer 6. The dimensions of the at least one output zone 18 of the front layer 6 corresponds to the dimensions of the at least one opening 16 in the first sound absorbing layer 8. The at least one output zone 18 may thus have a width between 80-120 centimeters and a height between 15-25 centimeters.

Between the cavity 10 and the first sound absorbing layer 8, as well as in the opening 16 of the first sound absorbing layer 8, a distribution layer 22 is arranged such that the purified air is discharged through the front layer 6 via the distribution layer 22. The distribution layer 22 may comprise a cellular plastic such as foam or a polyester resin, with an open cell structure and low density. The distribution layer 22 may comprise a material with a cell diameter of 2000 to 3500 micrometers. The open cell structure and the cell diameter of the distribution layer 22 results in a high permeability and low flow resistance and thus a limited pressure drop of the air flow when passing through the distribution layer 22. The distribution layer 22 and the first sound absorbing layer 8 are configured such that the flow resistance is lower and the permeability higher in the distribution layer 22 than in the first sound absorbing layer 8. This way, the purified air chooses to flow through the distribution layer 22. The flow resistance and the pressure drop cause the purified air to spread and to be distributed within and throughout the distribution layer 22. The low flow resistance also means that the air purifying device 12 may operate with low power and still achieve the desired flow rate, which minimizes the vibrations and noise from the air purifying device 12 itself. The thickness of the distribution layer 22 may be 10-25 millimeters. According to an aspect of the invention, the distribution layer 22 comprises air channels perpendicular to the extension of the front layer 6. The purified air is then led into the channels and flows in the direction towards the front layer 6. This way, the air flow at the output of the distribution layer 22 and at the at least one output zone 18 of the front layer 6, is directed substantially perpendicularly to the extension of the front layer 6. A substantially laminar air flow is thus achieved at the output of the distribution layer 22 and at the output of the front layer 6.

The inlet 14 to the cavity 10 comprises an aperture in the front layer 6 and the air purifying device 12 is tightly arranged at the front layer 6. The air purifying device 12 comprises at least one filter unit 24 and a fan means 26. The at least one filter unit 24 preferably comprises a particle filter which is adapted to filter particles of 0.01 micrometers and larger. Alternatively the filter unit 24 filters particles of 0.005 micrometers and larger. The filter unit 24 may be a panel filter. This way, most viruses, bacteria, asbestos fibre, ash, diesel particles, oil smoke, cement powder, the majority of tobacco particles and coal smoke are filtered out. The filtrating surface is dimensioned in relation to the total capacity and the air flow. The fan means 26 comprises a motor and a rotating arrangement of vanes or blades (not shown) and the capacity (m³/h) of the fan means 26 is dimensioned to achieve a local zone of pure air for a person located in the vicinity of the sound dampening device 1. The fan means 26 is preferably configured with accurately designed blades and a suitable number of blades in relation to the rotation frequency in order to reduce the vibration and thus the noise from the fan means 26. The air purifying device 12 also comprises a housing 28 surrounding the fan means 26, which housing 28 fits tightly against the front layer 6 such that no air can enter the inlet 14 to the cavity 10 without having passed through the at least one filter unit 24. A pre-filter 30 is preferably arranged in front of (upstream) the at least one filter unit 24, such that the polluted air first passes the pre-filter 30 and then the at least one filter unit 24. The pre-filter 30 is suitably a polyester resin with an open cell structure. The pre-filter 30 may have a cell diameter of 1500-2500 micrometers. The air purifying device 12 may further comprise an activated carbon filter, an ionisation filter, catalytic filter, and/or an ultraviolet sterilization unit. The air purifying device 12 preferably reduces the particle content of particles larger than 0.005 micrometers in the air by 70-99.9% and filtrates between 20-300 m$^3$ air per hour.

When the fan means 26 sucks in air (shown as arrows in the figure) from the surroundings it first passes the pre-filter 30 and it then passes through the at least one filter unit 24. The fan means 26 subsequently feeds the air into the cavity 10 and a pressure builds up inside the cavity 10, which pressure is higher than the pressure in the adjacent distribution layer 22. Since the rear layer 4 is impermeable and the distribution layer 22 is permeable the air flows through the distribution layer 22. Due to the porosity and thus the flow resistance of the distribution layer 22, the air flow is distributed throughout the distribution layer 22. Since the first sound absorbing layer 8 has a higher density and is less permeable than the distribution layer 22, the air chooses to flow through the distribution layer 22 arranged in the opening 16 of the first sound absorbing layer 8. The air is then discharged through an at least one output zone 18 in the front layer 6. Due to the low permeability of the first sound absorbing layer 8, the at least one output zone 18 corresponds to the opening 16 in the first sound absorbing layer 8, through which the air is flowing. This way, the flow area through which the purified air is discharged is larger than the cross sectional area of the cavity 10 and a substantially even distribution of purified air is achieved over a larger area.

The sound dampening device 1 may be attached on furniture, be integrated with furniture or be a separate unit arranged on walls, roofs or floor. This way, furniture with an integrated air purifying system for the local environment of the user of the furniture may be achieved. This type of furniture also has a positive effect on the noise level in a room. The sound dampening device 1 may constitute a module, such that several different sound dampening devices 1 may be arranged in fluid communication between their respective cavities 10. This modularity allows for the construction of the system capacity, in order to increase the surface with sound absorbing properties and flow area and air volume up to the desired levels. All the layers and components in the sound dampening device 1 may consist of recyclable material or natural fibre.

Figure 2:
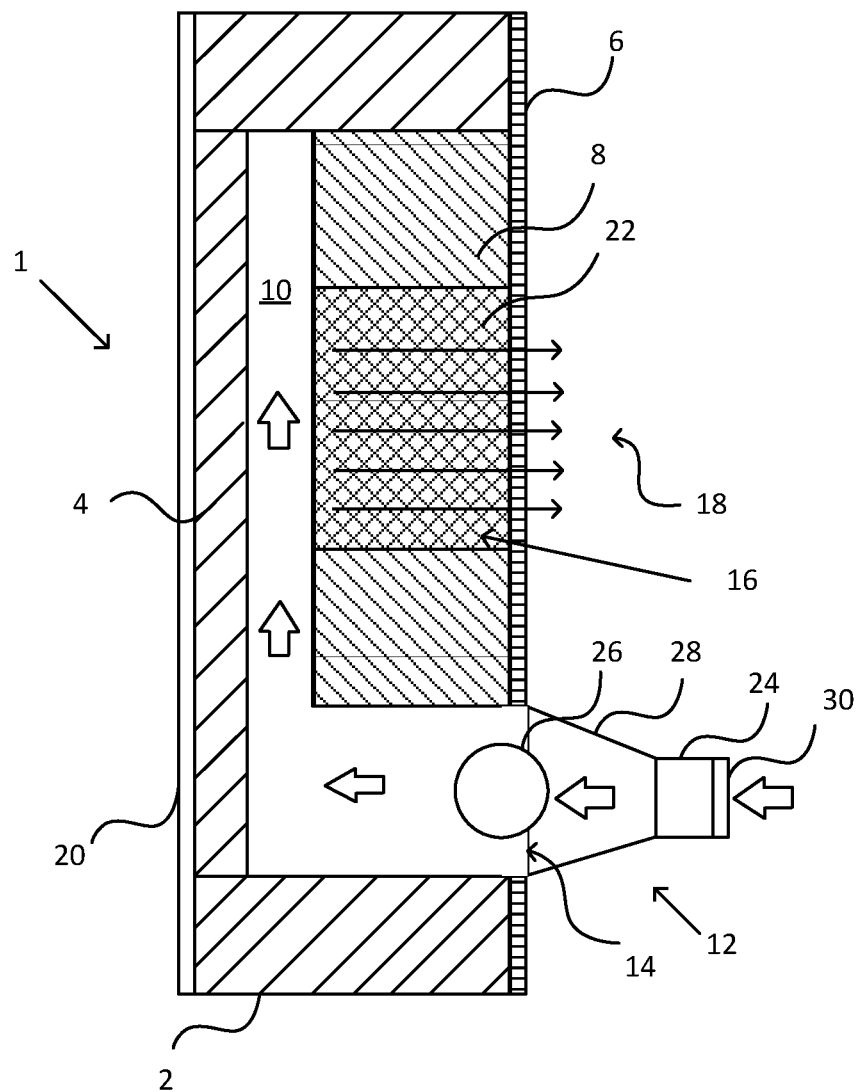
FIG. 2 shows a cross-sectional side view of a sound dampening device according to another embodiment of the present invention.

FIG. 2 shows a cross-sectional side view of a sound dampening device 1 according to an embodiment of the present invention. The sound dampening device 1 is configured as the sound dampening device 1 in FIG. 1, with the exception that the distribution layer 22 is arranged only in the opening 16 of the first sound absorbing layer 8. The function of the sound dampening device 1 in FIG. 2 and all other features are the same as described in relation to FIG. 1.

Figure 3A:
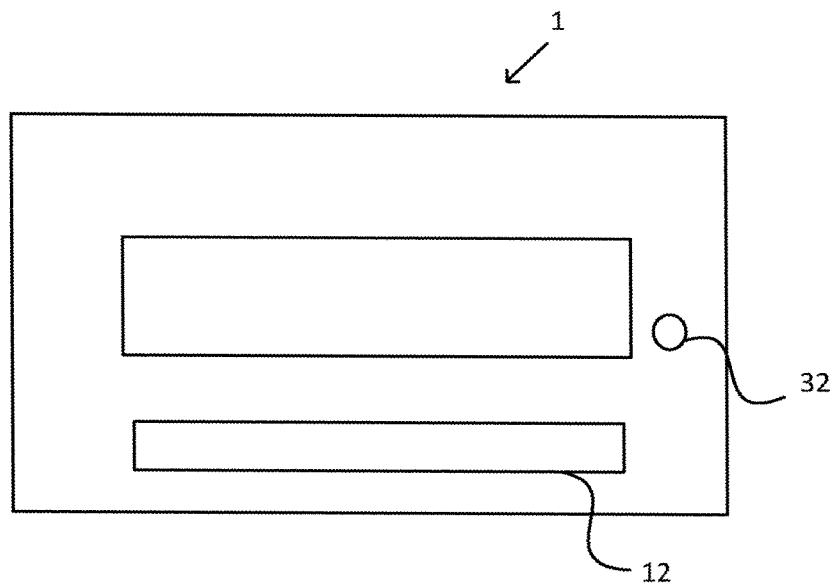
FIG. 3*a* shows a front view of a sound dampening device according to FIG. 1 or FIG. 2.

FIG. 3a shows a front view of the sound dampening device 1 according to FIG. 1 or FIG. 2. The inlet 14 to the cavity 10 and thus the air purifying device 12 is elongated and extends in the direction of the width of the sound dampening device 1. This way, a large air volume can be supplied to the cavity 10 without the need of operating the fan means 26 at high power. Also, by using an elongated filter unit 24 the filtrating area is increased which results in an improved filtering capacity. The at least one output zone 18 of the front layer 6 is shown with dotted lines. A regulating means 32 for regulating the air flow from the air purifying device 12 is arranged on an outer side of the front layer 6. The regulating means 32 may be a switch, lever, button, knob or similar and regulates the speed of the motor of the fan means 26. The motor may preferably work at different speeds and the lower the speed the less noise is generated. Preferably, a variable speed control of the fan means 26 motor is provided. Alternatively, the fan means 26 motor operates at three different speeds, a low speed, a medium speed and a high speed. A low speed may be defined as a speed lower than 650 rpm, a medium speed may be defined as a speed between 650-950 rpm and a high speed may be defined as a speed between 950-1310 rpm. Since the main object of the sound dampening device 1 is to improve the local environment there is no need for a very powerful and expensive fan means 26. This way, a cost-effective and less noisy sound dampening device is achieved. The sound dampening device may have a noise level under 40 dB(A), preferably under 30 dB(A), and a power consumption between 20-70 W, depending on the speed of the fan means 26 motor (not shown). By regulating the motor speed in combination with the porosity/permeability of the distribution layer 22 and/or the front layer 6, the purified air which is discharged through the front layer 6 has a flow rate between 0.1-0.5 m/s. This way draught is avoided and an optimal local environment with purified air is achieved.

Figure 3B:
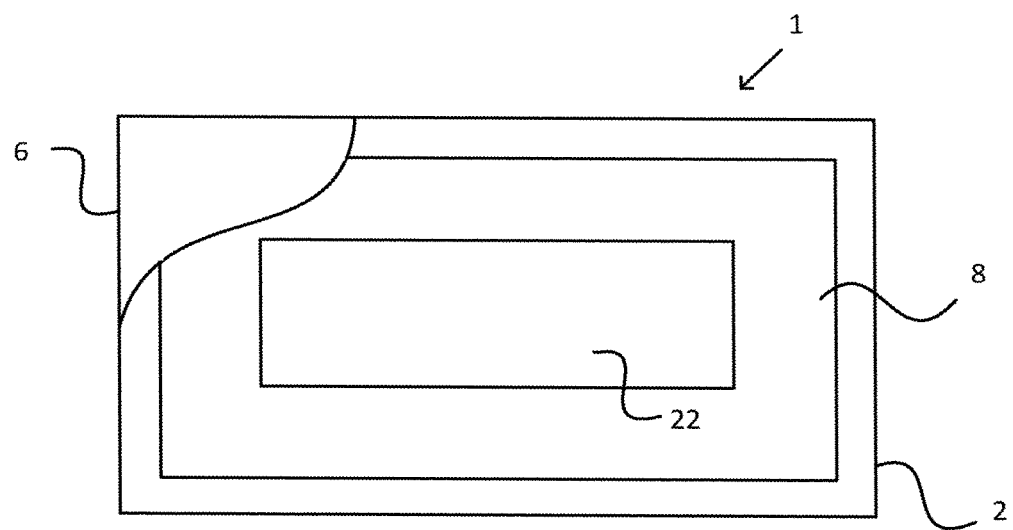
FIG. 3*b* shows a cross-sectional front view of a sound dampening device according to FIG. 1 or FIG. 2.

FIG. 3b shows a cross-sectional front view of the sound dampening device 1 according to FIG. 1, FIG. 2 or FIG. 3a. The frame 2 surrounds the first sound absorbing layer 8 and in the opening 16 of the first sound absorbing layer 8 the distribution layer 22 can be seen. The front layer 6 covers the front of the sound dampening device 1, which here is illustrated with only a portion of the front layer 6.

Figure 4:
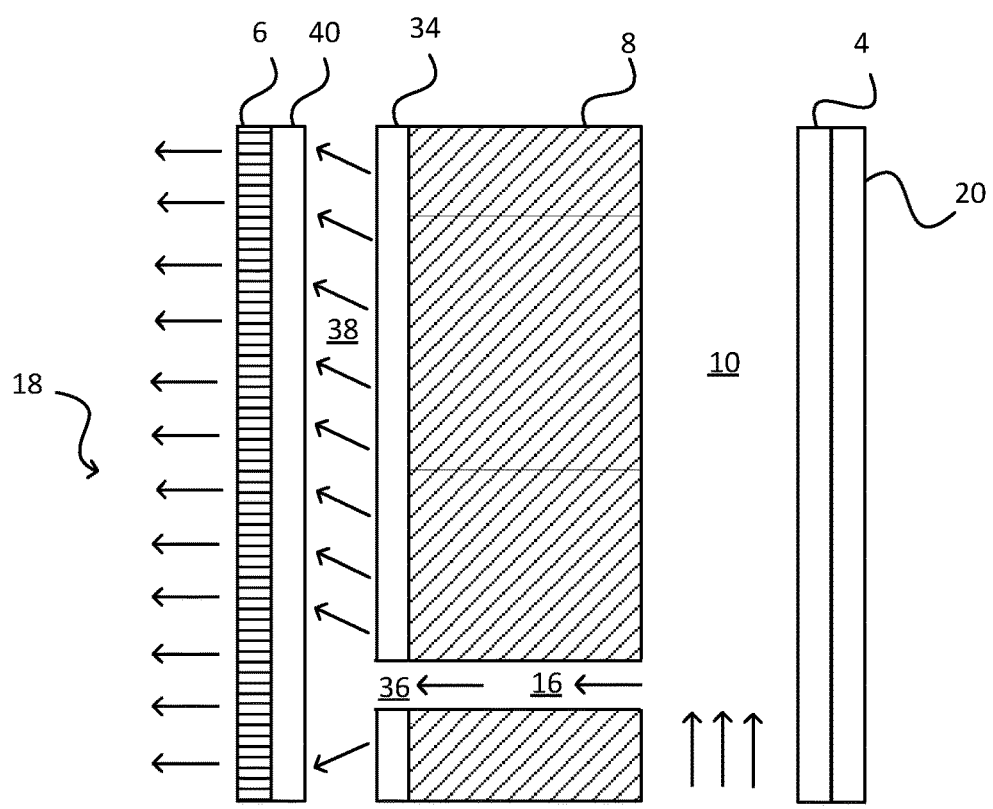
FIG. 4 shows a cross-sectional view of a sound dampening device according to an embodiment of the present invention.

FIG. 4 shows a cross-sectional view of a sound dampening device 1 according to an embodiment of the invention. The sound dampening device 1 comprises a frame 2 (not shown), a rear layer 4 and a front layer 6 arranged on opposite sides of the frame 2, such that the frame 2, the rear layer 4 and the front layer 6 forms an enclosed space. A first sound absorbing layer 8 is also arranged between the rear layer 4 and the front layer 6 wherein a cavity 10 is formed between the rear layer 4 and the first sound absorbing layer 8. An air purifying device 12 is arranged in fluid communication with the cavity 10, such that purified air from the air purifying device 12 is supplied to the cavity 10 via an inlet 14 and is discharged through at least one opening 16 in the first sound absorbing layer 8 and at least one output zone 18 in the front layer 6.

The density of the front layer 6 is between 20-50 kg/m$^3$, preferably between 30-40 kg/m$^3$. This way, the front layer 6 causes a low air resistance and the purified air is discharged through the front layer 6 with an optimal speed. The front layer 6 may comprise a fabric with low air resistance. The front layer 6 may comprise a fabric with a polyether foam coating. The thickness of the front layer 6 is between 2-10 millimeters, preferably between 4-8 millimeters.

The rear layer 4 preferably comprises an impermeable material, preferably a wooden board, cardboard, fibre board or similar. On an outer side of the rear layer 4, a second sound absorbing layer 20 is arranged.

The first sound absorbing layer 8 may consists of a resistive sound absorber. It may be a wadding of thermal bonded polyester fibre with a thickness between 10-50 millimeters. The weight per unit area of the first sound absorbing layer 8 is between 1000-1500 g/m². The at least one opening 16 in the first sound absorbing layer 8 may have the shape of a rectangle or any other shape. Due to lower flow resistance, the purified air passes through the opening 16 in the first sound absorbing layer 8.

A first membrane 34 is arranged between the first sound absorbing layer 8 and the front layer 6, such that it abuts the first sound absorbing layer 8. The first membrane 34 comprises an opening 36, corresponding to the opening 16 in the first sound absorbing layer 8. The first membrane 34 preferably consists of a material which is air impermeable and has mechanical features which does not hinder the transfer of sound to the first sound absorbing layer 8. The first membrane 34 may for example be a completely airtight polyamide coated with polyurethane, with a weight of 600 g/m².

An air distribution chamber 38 is formed between the first membrane 34 and the front layer 6, which chamber 38 acts sound dampening. The purified air passes through the opening 16 in the first sound absorbing layer 8 and the opening 36 in the first membrane 34 and fills the chamber 38. A distance material with a very open structure may be arranged in the distribution chamber 38, which enables distribution of pure air with limited pressure drop. The distance material may be a three-dimensional polyester fabric with a thickness between 10 to 30 millimeters, a very low density and low weight per cubic meter (10-20 kg).

A second perforated membrane 40 is arranged between the front layer 6 and the chamber 38, such that the purified air passes through the perforated membrane 40 and on through the front layer 6. The dimensioning of the number of holes and the sizes of the holes per unit of area in the membrane 40 is inversely proportional to the pressure gradient at the inlet into the chamber 38, in order to distribute the air flow evenly over the front layer 6. The perforation comprises more holes further away from the fan means 26 of the air purifying device 12. The perforation pattern of the membrane 40 may for example comprise between 2000 to 4000 holes/m² with a diameter between 3 to 10 millimeters.

The air purifying device 12 comprises at least one filter unit 24 and a fan means 26 which are configured and functions as described in relation to FIG. 1. Structural components, sound absorbers and air channels (the cavity 10 and the air distribution chamber 38) are configured to dampen the sound frequencies that are generated from the fan means 26 and from the air flow itself in an efficient way. The capacity (m³/h) of the fan means 26 is dimensioned after the at least one output zone 18 in the front layer, the at least one filter unit 24 and the requested volume of purified air in relation to the number of persons and the air volume indoors, amongst other parameters.

The fan means 26 feeds the purified air into the cavity 10 and a pressure builds up inside the cavity 10. Since the rear layer 4 is impermeable the air flows through the opening 16 in the first sound absorbing layer 8 and the opening 36 in the first membrane 34 to the air distribution chamber 38. The air is then distributed over the perforated membrane 40 and is discharged through the at least one output zone 18 in the front layer 6. The permeability of the different components and the distribution of air pressure mean that the pressure of the air discharged through the front layer 6 is lower than the pressure in the distribution chamber 38, which is lower than the air pressure in the opening 16 in the first sound absorbing layer 8. This way, the flow area through which the purified air is discharged is larger than the cross sectional area of the cavity and a substantially even distribution of purified air is achieved over a larger area.

The sound dampening device 1 may be attached on furniture, be integrated with furniture or be a separate unit arranged on walls, roofs or floor. The sound dampening device 1 may constitute a module, such that several different sound dampening devices may be arranged in fluid communication between their respective cavities. This modularity allows for the construction of the system capacity, in order to increase the surface with sound absorbing properties and flow area and air volume up to the desired levels. All the layers and components in the sound dampening device 1 may consist of recyclable material or natural fibre.

Figure 5:
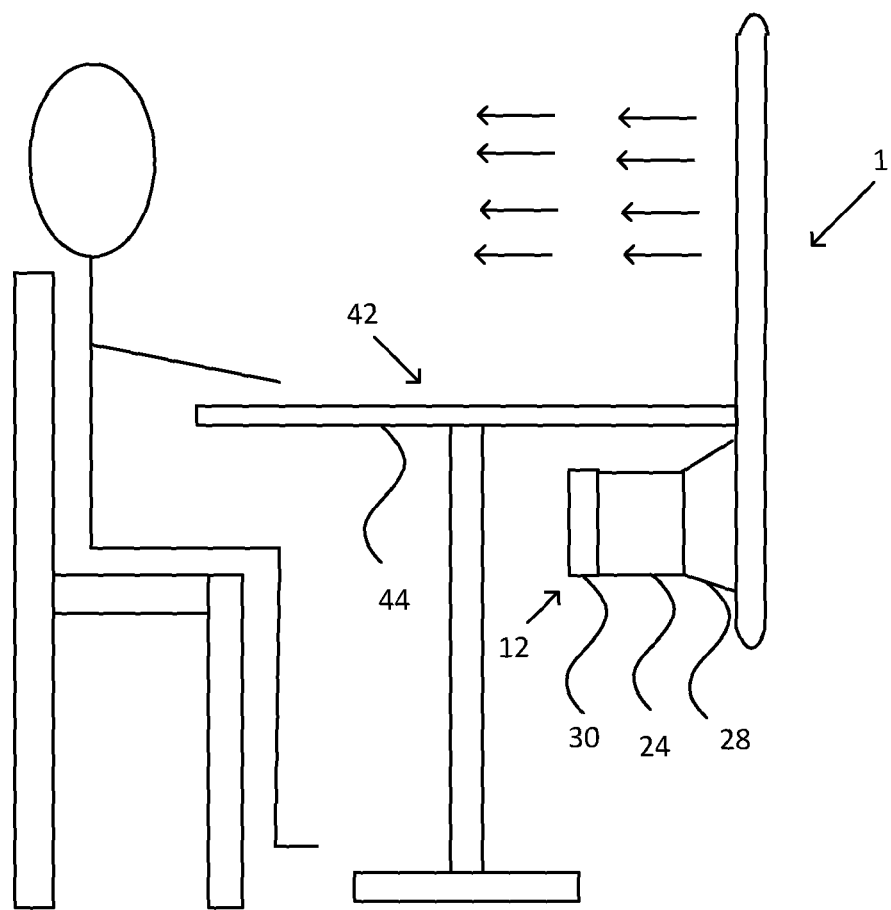
FIG. 5 shows a side view of a sound dampening device according to FIG. 1, FIG. 2 or FIG. 4 constituting an acoustic screen.

FIG. 5 shows a side view of a sound dampening device 1 according to FIG. 1, FIG. 2 or FIG. 4, where the sound dampening device 1 constitutes an acoustic screen, partition wall or similar. The sound dampening device 1 is thus arranged at a desk 42, such that the air purifying device is positioned under the desktop 44. The sound dampening device 1 constituting an acoustic screen may have a width of 800-2200 millimeters and a height of 600-1000 millimeters. The thickness of the sound dampening device 1 may be 30-60 millimeters. The sound dampening device 1 is preferably arranged, such that the lower edge of the at least one output zone 18 of the front layer 6 is positioned 10-25 centimeters above the desktop 44. The different layers and/or membranes are configured such that the purified air is discharged through the front layer 6 at a level corresponding substantially to the level of a person's head. Thus is achieved a pure local environment and a good acoustic environment which improves the comfort of the person and which also affects the person's health and concentration in a positive way.

Figure 6A:
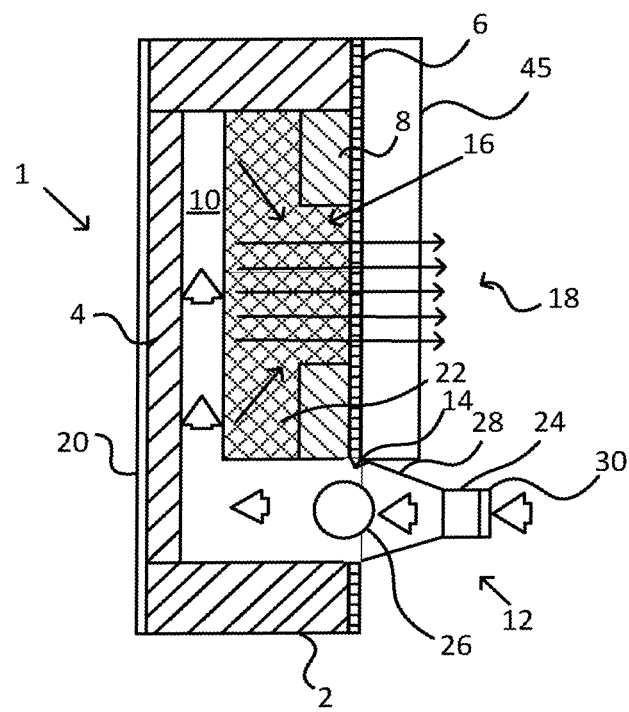
FIG. 6*a* shows a cross-sectional side view of a sound dampening device according to an embodiment of the present invention.

FIG. 6a shows a cross-sectional side view of a sound dampening device 1 according to FIG. 1, with the addition of an air permeable padded layer 45 arranged on an outer side of the front layer 6, above the aperture in the front layer 6 and the air purifying device 12. This way, the sound dampening device 1 is soft and comfortable to lean against. The padded layer 45 may comprise a cellular plastic such as foam or a polyester resin, with an open cell structure and low density. The padded layer 45 may comprise a material with a cell diameter between 1500 to 2500 micrometers. The open cell structure and the cell diameter results in a high permeability/porosity and the padded layer 45 barely affects the flow rate of the purified air. The padded layer 45 may comprise any other material with equivalent properties relating to resistance and permeability. The thickness of the padded layer 45 may be 20-50 millimeters. The padded layer 45 may consist of wadding covered by a fabric with high permeability. The purified air is thus discharged through the distribution layer 22, the at least one opening 16 in the first sound absorbing layer 8, the front layer 6 and finally the padded layer 45. The area of the padded layer 45 where purified air is discharged corresponds to the at least one output zone 18 of the front layer 6.

Figure 6B:
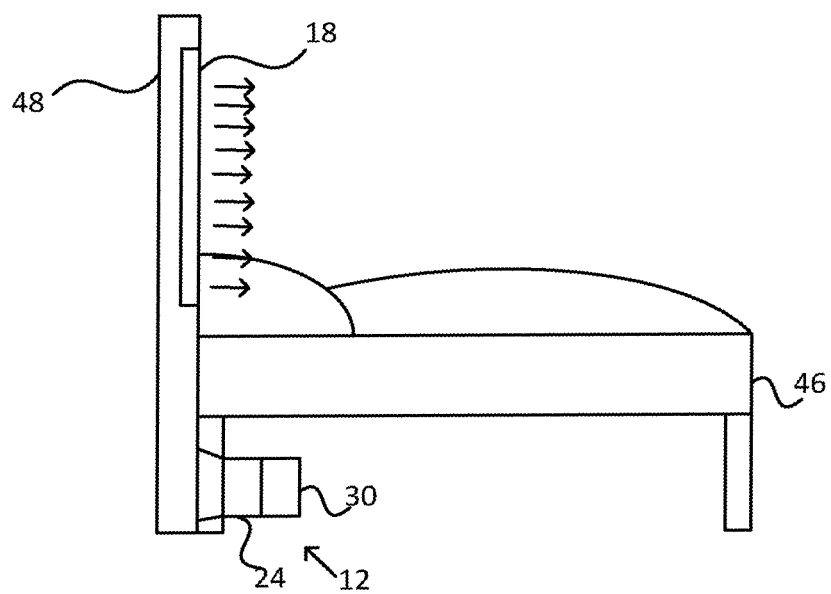
FIG. 6*b* shows a side view of a headboard configured according to the sound dampening device in FIG. 1, FIG. 2, FIG. 4 of FIG. 6*b*.

FIG. 6b shows a side view of a headboard device 48 comprising a frame 2, a rear layer 4 and a front layer 6 arranged on opposite sides of the frame 2, such that the frame 2, the rear layer 4 and the front layer 6 forms an enclosed space, wherein a first intermediate layer 8 is arranged between the rear layer 4 and the front layer 6. A cavity 10 is formed between the rear layer 4 and the intermediate layer 8 and an air purifying device 12 is arranged in fluid communication with said cavity 10, such that purified air from the air purifying device 12 is supplied to the cavity 10 via an inlet 14 and is discharged through at least one opening 16 in the intermediate layer 8 and at least one output zone 18 in the front layer 6. The first intermediate layer 8 is preferably a sound absorbing layer.

An air permeable distribution layer 22 is arranged in the at least one opening 16 in the intermediate layer 8, such that the purified air is discharged through the front layer 6 via the distribution layer 22. According to an aspect of the invention the distribution layer 22 comprises air channels perpendicular to the extension of the front layer 6. The air purifying device 12 comprises at least one filter unit 24 and fan means 26. An air permeable padded layer 45 as disclosed in FIG. 6b is preferably arranged on an outer side of the front layer 6. A regulating means 32 for regulating the air flow from the air purifying device 12 is also arranged on an outer side of the front layer 6. A second sound absorbing layer 20 is preferably arranged at an outer side of the rear layer 4. The features, properties and functions of the different layers and components of the headboard device 48 are the same as the features, properties and functions of the same components described in relation to the sound dampening device 1 disclosed in FIG. 1-6b.

According to an aspect of the invention, the headboard device 48 comprises a sound dampening device 1 as previously disclosed in FIG. 1-4 or 6a.

The headboard device 48 is arranged by a bed 46, such that the air purifying device 12 is positioned under the bed 46 and the at least one output zone 18 is positioned above the bed 46. The sound from the air purifying device 12 is thus further dampened by the bed 46. Cold air is heavier than warm air and the air at the floor level in a room is thus colder than the air on a higher level in the room. The difference of temperature in a room may vary between 0.2-2 degrees between different levels. By arranging the headboard 48 with the air purifying device 12 close to the floor under the bed 46, colder air will enter the headboard 48. When the purified air is discharged through the front layer 6 and the padded layer 45 it will fall downwards since it is colder than the surrounding air at the same level and thus has a higher density. This way the natural temperature difference in a room is taken advantage of and it is ensured that the purified air is supplied and stays in the vicinity of the person lying on the bed 46. The at least one opening 16 in the first sound absorbing layer 8 and thus the at least one output zone 18 (here shown with dotted lines) in the front layer 6 is preferably configured such that purified air is discharged over 70-90% of the total area of the padded layer 45. Purified air is preferably discharged from the headboard 48 adjacent the mattress of the bed 46. This way purified air is discharged close to the persons head laying in the bed 46, and a local environment with purified air is achieved. By configuring the headboard device 48 such that purified air may be discharged over a large area, enough purified airflow is achieved even in the case where part of the output zone 18 is covered by for example a pillow or a person.

The air purifying device 12 preferably comprises a pre-filter 30 arranged in front of the at least one filter unit 24. The pre-filter 30 preferably comprises a screen, to prevent dust and dirt from entering the at least one filter unit 24. The pre-filter 30 suitably comprises a polyester resin with an open cell structure. The pre-filter 30 may comprise a material with a cell diameter of 1500-2500 micrometers.

There are higher requirements regarding sound level in a bedroom than in other environments and the headboard device 48 may thus generate a noise level under 30 dB(A), preferably under 25 dB(A).

The headboard device 48 may also comprise speakers, lightening, compartments or shelves and/or electrical sockets integrated in the headboard device 48. This way is achieved a functional headboard device 48, which is sound dampening and provides a pure local environment. Good air quality in a bedroom may improve the sleep and may thus improve people's health.

The headboard device 48 may have a width of 700-2200 millimeters and a height of 900-1300 millimeters. The thickness of the headboard device 48 may be 30-250 millimeters.

The present invention should not be limited to the above-described embodiments, but modifications and combinations thereof can occur within the invention.

What is claimed is:

1. A sound dampening device comprising:
a frame,
a rear layer and a front layer arranged on opposite sides of the frame, such that the frame, the rear layer and the front layer forms an enclosed space, and
a first sound absorbing layer arranged between the rear layer and the front layer,
wherein a cavity is formed between the rear layer and the first sound absorbing layer and an air purifying device is arranged in fluid communication with said cavity, such that purified air from the air purifying device is supplied to the cavity via an inlet and is discharged through at least one opening in the first sound absorbing layer and at least one output zone in the front layer,
wherein an air permeable distribution layer is arranged in the at least one opening in the first sound absorbing layer, such that the purified air is discharged through the front layer via the distribution layer,
wherein the first sound absorbing layer and the distribution layer are configured such that the permeability is higher and the flow resistance is lower in the distribution layer than in the first sound absorbing layer.

2. The sound dampening device according to claim 1, wherein the distribution layer comprises a material with a cell diameter of 2000-3500 micrometers.

3. The sound dampening device according to claim 1, wherein the distribution layer comprises air channels perpendicular to an extension of the front layer.

4. The sound dampening device according to claim 1, wherein the first sound absorbing layer has a weight per area unit between 1000-1500 g/m$^2$.

5. The sound dampening device according to claim 1, wherein the front layer has a weight per area unit between 150-350 g/m$^2$.

6. The sound dampening device according to claim 1, wherein the air purifying device comprises at least one filter unit and fan means.

7. The sound dampening device according to claim 1, wherein the inlet to the cavity comprises an aperture in the front layer.

8. The sound dampening device according to claim 7, wherein the air purifying device is tightly arranged at the front layer.

9. The sound dampening device according to claim 1, wherein a second sound absorbing layer is arranged at an outer side of the rear layer.

10. The sound dampening device according to claim 1, wherein an air permeable padded layer is arranged on an outer side of the front layer.

11. The sound dampening device according to claim 1, wherein a regulating means for regulating the air flow from the air purifying device is arranged on an outer side of the front layer.

12. The sound dampening device according to claim 1, wherein the rear layer comprises a fibre board.

13. The sound dampening device according to claim 1, wherein the sound dampening device constitutes a partition wall or an acoustic screen.

14. A headboard device comprising the sound dampening device according to claim 1.

15. A headboard device comprising:
 a frame,
 a rear layer and a front layer arranged on opposite sides of the frame, such that the frame, the rear layer and the front layer forms an enclosed space, and
a first sound absorbing layer arranged between the rear layer and the front layer,
  wherein a cavity is formed between the rear layer and the sound absorbing layer and an air purifying device is arranged in fluid communication with said cavity, such that purified air from the air purifying device is supplied to the cavity via an inlet and is discharged through at least one opening in the sound absorbing layer and at least one output zone in the front layer,
 wherein an air permeable distribution layer is arranged in the at least one opening in the first sound absorbing layer, such that the purified air is discharged through the front layer via the distribution layer,
 wherein the first sound absorbing layer and the distribution layer are configured such that the permeability is higher and the flow resistance is lower in the distribution layer than in the first sound absorbing layer.

16. The headboard device according to claim 15, wherein the distribution layer comprises air channels perpendicular to the extension of the front layer.

17. The headboard device according to claim 15, wherein the air purifying device comprises at least one filter unit and fan means.

18. The headboard device according to claim 15, wherein an air permeable padded layer is arranged on an outer side of the front layer.

19. The headboard device according to claim 15, wherein a regulating means for regulating the air flow from the air purifying device is arranged on an outer side of the front layer.

20. The headboard device according to claim 15, wherein the headboard device is configured such that when it is arranged by a bed, the air purifying device is positioned under the bed and the at least one output zone is positioned above the bed.

* * * * *